United States Patent
Geller et al.

(10) Patent No.: US 9,084,528 B2
(45) Date of Patent: Jul. 21, 2015

(54) PHASE CONTRAST IMAGING

(75) Inventors: Dieter Geller, Aachen (DE); Klaus Juergen Engel, Aachen (DE); Gereon Vogtmeier, Aachen (DE); Thomas Koehler, Norderstedt (DE); Ewald Roessl, Ellerau (DE)

(73) Assignee: Koninklijke Philips N.V., Eindhoven (NL)

( * ) Notice: Subject to any disclaimer, the term of this patent is extended or adjusted under 35 U.S.C. 154(b) by 11 days.

(21) Appl. No.: 13/514,682

(22) PCT Filed: Dec. 3, 2010

(86) PCT No.: PCT/IB2010/055561
§ 371 (c)(1),
(2), (4) Date: Jun. 8, 2012

(87) PCT Pub. No.: WO2011/070488
PCT Pub. Date: Jun. 16, 2011

(65) Prior Publication Data
US 2012/0243658 A1    Sep. 27, 2012

(30) Foreign Application Priority Data
Dec. 10, 2009 (EP) .................... 09178701

(51) Int. Cl.
*G01N 23/04* (2006.01)
*A61B 6/00* (2006.01)

(52) U.S. Cl.
CPC .............. *A61B 6/00* (2013.01); *A61B 6/4291* (2013.01); *A61B 6/484* (2013.01); *A61B 6/4441* (2013.01)

(58) Field of Classification Search
CPC ............... A61B 6/484; A61B 6/4291
USPC ........................................ 378/16, 62
See application file for complete search history.

(56) References Cited

U.S. PATENT DOCUMENTS 5,745,665 A * 4/1998 Pasco ........................... 345/427
7,924,973 B2 * 4/2011 Kottler et al. .................. 378/36
(Continued)

FOREIGN PATENT DOCUMENTS

| | | |
|---|---|---|
| CN | 101044987 A | 10/2007 |
| EP | 1731099 A1 | 12/2006 |
| EP | 1879020 A1 | 1/2008 |
| EP | 2395905 A1 | 12/2011 |
| WO | 2010092513 A1 | 8/2010 |

OTHER PUBLICATIONS

Bech et al, "Soft-Tissue Phase-Contrast Tomography With an X-Ray Tube Source", Phys Med Biol, vol. 54, 2009, pp. 2747-2753.
(Continued)

*Primary Examiner* — Glen Kao
*Assistant Examiner* — Danielle Fox

(57) ABSTRACT

X-ray devices for Phase Contrast Imaging (PCI) are often built up with the help of gratings. For large field-of-views (FOV), production cost and complexity of these gratings could increase significantly as they need to have a focused geometry. Instead of a pure PCI with a large FOV, this invention suggests to combine a traditional absorption X-ray-imaging system with large-FOV with an insertable low-cost PCI system with small-FOV, The invention supports the user to direct the PCI system with reduced FOV to a region that he regards as most interesting for performing a PCI scan thus eliminating X-ray dose exposure for scanning regions not interesting for a radiologist. The PCI scan may be generated on the basis of local tomography.

15 Claims, 3 Drawing Sheets

(56) References Cited

U.S. PATENT DOCUMENTS

| | | | |
|---|---|---|---|
| 8,855,265 B2 | 10/2014 | Klaus et al. | |
| 2004/0131145 A1 | 7/2004 | Ohara | |
| 2004/0258195 A1* | 12/2004 | Hara | 378/11 |
| 2006/0056581 A1* | 3/2006 | Hoffman et al. | 378/19 |
| 2006/0104406 A1* | 5/2006 | Siltanen et al. | 378/4 |
| 2007/0183559 A1* | 8/2007 | Hempel | 378/4 |
| 2007/0183562 A1* | 8/2007 | Popescu et al. | 378/19 |
| 2007/0183584 A1* | 8/2007 | Baumann et al. | 378/145 |
| 2008/0002209 A1* | 1/2008 | Yaqoob et al. | 356/490 |
| 2010/0272235 A1* | 10/2010 | Takahashi | 378/62 |

OTHER PUBLICATIONS

Pfeiffer et al, "High-Resolution Brain Tumor Visualization Using Three-Dimensional X-Ray Phase Contrast Tomography", Phys. Med. Biol., vol. 52, 2007, pp. 6923-6930.

Katsevich, Improved Cone Beam Local Tomography, Inverse Problems, vol. 22, 2006, pp. 627-643.

Pfeiffer et al, "Hard X-Ray Phase Tomography With Low-Brilliance Sources", Physical Review Letters, vol. 98, 2007, pp. 108105-1-108105-4.

Pfeiffer et al, "Phase Retrieval and Differential Phase-Contrast Imaging With Low Brilliance X-Ray Source", Nature Physics, vol. 2, 2006, pp. 258-261.

Pfeiffer et al, "Shearing Interferometer for Quantifying the Coherence of Hard X-Ray Beams", Physical Review Letters, vol. 94, 2005, pp. 164801-1-164801-4.

Weitkamp et al, "X-Ray Phase Imaging With a Grating Interferometer", Optics Express, vol. 13, No. 16, 2005, pp. 6296-6304.

* cited by examiner

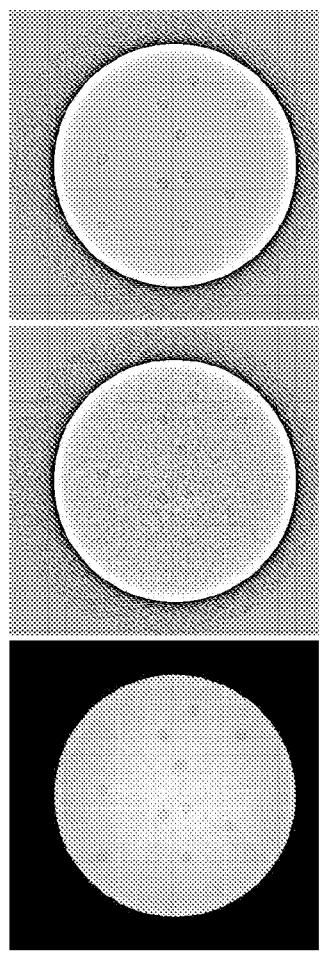
FIG. 3A
FIG. 3B
FIG. 3C
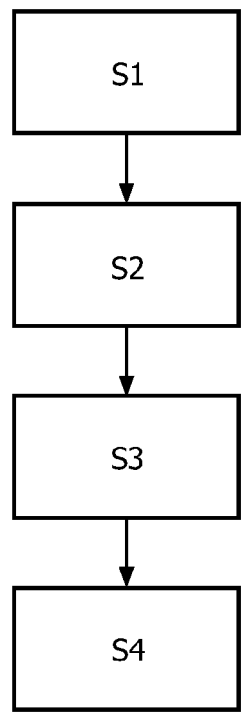
FIG. 4

PHASE CONTRAST IMAGING

FIELD OF THE INVENTION

The invention relates to differential phase contrast imaging (PCI). In particular, the invention relates to a device and method for differential phase contrast imaging.

BACKGROUND OF THE INVENTION

The traditional X-ray systems used for medical applications are mainly based on the different absorption of X-rays in matter resulting in projection images formed by the accumulated absorption of the X-rays along a line. Yet, matter does not only influence the absorption but also the refraction of X-rays. This characteristics promises higher X-ray contrast between human tissue types than the conventional absorption-based imaging and hence can represent a future improvement. A possible setup for facilitating PCI is based on gratings.

The use of gratings within the transmitted X-ray beam face the problem, that non-focused gratings produce a less modulated absorption by themselves especially outside of the central region of the field-of-view (FOV), resulting in a decreased visibility of an interference pattern, a decreased transmitted mean intensity, and thus a lower signal-to-noise ratio at a detector. Therefore, the absorption image has either lower contrast-to-noise ratio or the radiation dose must be increased which the human body is potentially harmfully exposed. For the same reason, a typically non-focused source grating limits the FOV which can be exploited effectively by the PCI system. This last aspect is caused by both the thickness of the source grating necessary for producing a minimal absorption for the X-rays and the slit width needed to filter out sufficiently coherent beams. All that leads to a decreased mean X-ray intensity and a decreased visibility of the interference pattern for locations in the resulting image outside the centre of the FOV.

A problem of differential phase contrast CT is that wrapping of the phase gradient occurs at the rim of the object. Different methods to unwrap the phase gradient have been proposed already, improving overall image quality substantially, but nevertheless, none of them works perfectly. Another approach is to avoid the phase wrapping by means of additional hardware. A further drawback of differential phase contrast CT is the fact that the noise power spectrum of the image has a peak for low frequencies. The problem here is that low-frequency noise is perceived more annoying than high frequency noise.

SUMMARY OF THE INVENTION

The invention targets in improving an X-ray system based on phase contrast imaging (PCI).

This is achieved by the subject matter of each of the independent claims. Further embodiments of the invention are described in the respective dependent claims.

According to the invention, a physician may be enabled to target the limited field of view (FOV) of a PCI system to a desired location. This location may be selected with the help of a previous pure absorption scan with a large FOV by moving the grating arrangement out of the X-ray beam. This previous scan can be performed with a lower intensity compared to conventional absorption-based scanning thus reducing the X-ray dose exposure to the object to scan.

In general, a device for phase contrast imaging of an object according to a first embodiment of the invention, comprises a source for an X-ray beam, a detector for detecting the X-ray beam, a grating arrangement, and a processing unit for controlling the phase contrast imaging, wherein the grating arrangement is movable out of the X-ray beam.

Alternatively, a device for phase contrast imaging of an object according to a second embodiment of the invention comprises a source for an X-ray beam, a detector for detecting the X-ray beam, a grating arrangement, and a processing unit for controlling the phase contrast imaging, wherein the processing unit is adapted to perform a local tomography.

It is noted that 'object' in the context of the invention may refer to a dead or living human or animal body or to a plant or portion of a plant. Furthermore, it may stand for an artificial part like a machine part or an assembly of parts, wherein these parts may be made out of one or more materials like metal, ceramic or plastic materials.

According to a further embodiment of the invention, the device is capable of generating volumetric images of the object. That is, the device may be based, for example, on a source-detector combination which is capable to rotate around the object, for 3D-X-ray imaging. On the other hand, the source and the detector may be located on separate devices to allow also a movement of one of the source and detector. Furthermore, the source and detector may be fixed wherein the object will be located on a rotatable carrier.

According to another embodiment, the grating arrangement may include a source grating G0, a diffracting grating G1 and an analyzer grating G2, wherein the source grating is located between the source and the object, and wherein the diffracting grating and the analyzer grating are located between the object and the detector. However, it may also be possible to perform a PCI imaging without the source grating G0, i.e. only with the diffracting grating G1 and the analyzer grating G2.

The gratings of the grating arrangement may be mounted on one slider to facilitate the movement of the complete grating arrangement out of the X-ray beam. However, the gratings G0, G1 and G2 may also be mounted on more than one slider so that also a separate or independent movement of the gratings may be realized.

In accordance with a further embodiment, the width of the grating arrangement is smaller than the width of the X-ray beam, so that a portion of the X-ray beam passes through the grating arrangement, when the grating arrangement is located within the X-ray beam. The grating arrangement may be movable within the X-ray beam in a plane perpendicular to a main direction of the X-ray beam, to allow a positioning of the grating arrangement within the FOV. On the other hand, the grating arrangement may be moved in the main direction of the X-ray beam to allow for a zoom of the PCI image.

Furthermore, the device according to the invention may comprise a variable aperture by means of which the width of the X-ray beam is adaptable to the width and the position of the grating arrangement.

It is noted, that the width of the grating arrangement may be substantially smaller than the width of the X-ray beam. By means of the variable aperture, it is also possible to reduce the width of the X-ray beam so that the X-ray beam passes only the grating arrangement or even a sub-portion of the grating arrangement. Thus, only a small portion of the object within the X-ray beam may be subjected to a radiation. The possibility of moving or changing the position of the grating arrangement within the field of view of the X-ray beam provides for an appropriate positioning of the grating arrangement to a region of interest, and on the other hand for a reduction of radiation to which an object is subjected.

According to a further embodiment, the device may further comprise a monitor for visualizing the position of the grating arrangement. Additionally, the device according to the invention may comprise an input device by means of which the position of the grating arrangement is controllable. In other words, a user of the device may choose a region of interest in an X-ray image generated without a grating arrangement, and may shift a frame on the monitor to said region of interest, wherein the frame refers to the field of view through the grating arrangement.

The setup of a device for phase contrast imaging may be sketched as following:

The gratings G0, G1, and G2 may be mounted on a movable slider whose movement may be controlled by a step motor that allows movements in the x,y-plane, i.e., perpendicular to the main direction of the X-ray beam path.

The step motors may be controlled by a software program that may be able to visualize the current position of the arrangement of gratings on a screen in a synchronous way.

The X-ray source may be mounted on a second slider that may be moved synchronously to the first slider but should be not activated when the first slider drives the gratings out of the X-ray path.

According to another aspect of the invention, a method for phase contrast imaging of an object in accordance with a first embodiment comprises the step of moving a grating arrangement between a source for an X-ray beam, an object and a detector, so that a source grating of the grating arrangement is located between the source and the object, a diffracting grating and an analyzer grating of the grating arrangement are located between the object and the detector, and so that a portion of the X-ray beam passes through the grating arrangement.

Furthermore, another method for phase contrast imaging of an object according to a second embodiment, comprises the steps of generating signals by means of a detector for detecting an X-ray beam, wherein a portion of the object is located together with a grating arrangement within the X-ray beam between a source for the X-ray beam and the detector, performing a local processing of the signals from the detector, and generating an image based on the processed signals, wherein the step of performing a local processing may include a qualitative assessment of adjacent detector pixels.

Here, qualitative assessment may include a calculation of the first derivative of the signals by calculating the difference of the signal of two adjacent pixels of the detector array. The local tomography aims in visualizing contours of internal structures of the object. In other words, the proposed method enhances the possibility to tell the difference between structures, instead of presenting a representation of the quantitative measurements of each single detector pixel.

The method according to the second embodiment of the invention can even handle heavily truncated projection data and thus is well-suited for region of interest tomography.

According to another aspect of the method, the relative motion between the object and the system may be chosen such that the gratings are perpendicular to the projected source trajectory.

Furthermore, the step of performing a local processing may include a pixel-wise phase gradient retrieval and a calculating of a derivative of the phase gradient.

According to a further embodiment of the method, the generation of an image is performed using a weighted back-projection of the locally processed signals from the detector (D).

According to a further embodiment, the method may further comprise the steps of generating an image of a portion of the object without the grating arrangement in the X-ray beam, and generating an image of a portion of the object with the grating arrangement within the X-ray beam, wherein the grating arrangement may be moved in a plane perpendicular to a main direction of the X-ray beam.

The method may further comprise the step of shifting at least one of the gratings for carrying out a phase stepping approach.

Performing the method of the invention, or utilizing a device according to the invention, a two-step approach is proposed.

At first, a common absorption-based image with a large FOV is produced. This image is generated by driving the arrangement of the three gratings G0, G1, and G2 that may be mounted on a movable slider out of the X-ray beam. The setup thus delivers an image that is not deteriorated by the limitations of the gratings in any way and delivers an absorption image of the radiated body with no reduction of the FOV identical to common absorption imaging.

In a second step the grating arrangement is moved back, i.e., is inserted into the setup by, e.g., a step motor. The position where the grating arrangement is inserted can be controlled. Hence, it is possible to indicate this position within the previously produced absorption image directly on a screen in form of a frame covering the same region that the system of gratings affects in a synchronous way. The physician who performs the X-ray scan may be able to choose the exact position of the centre of this frame on the screen and can thus position that frame to a region-of-interest (ROI) that he is most interested in because the absorption image indicates a potential abnormality there. At this position the grating arrangement is synchronously inserted into the X-ray path to now produce a PCI image of this ROI. This allows the physician to receive a PCI image focused on that ROI with higher contrast-to-noise ratio without further increasing the X-ray dose exposed to the human body. The physician might decide to reduce the exposure in the first step if it is clear that the first step is only required to allow a positioning of the grating arrangement in the second step.

The directing of the FOV to a ROI results in a second advantage of the subject matter of the invention. From the absorption image that is more extended in size it is possible to roughly determine the predominant tissue type that can be expected within the ROI with the help of a list of absorption coefficients of for example typical human tissue types that the application is designed for. To this end also automatic segmentation algorithms applied online to the ROI may be helpful. This information allows the optimization of the energy of the X-ray source for the following PCI scan together with the distance between G1 and G2—the Talbot distance—that are both related with the wavelength of the X-ray light. The optimization of the wavelength-related parameters may increases the quality of the resulting PCI image remarkably. The Talbot distance may be modified in a similar way as done for the whole arrangement of the three gratings.

The invention can be used with any type of a PCI system where the FOV represents a limiting factor, for mammography, cardiac or head surgery systems, or computed tomography if the reconstruction is performed sufficiently fast so that the result can be visualized directly after the scan on a screen.

According to a further aspect of the invention, a computer program for phase contrast imaging is provided which, when executed on a processing unit of the device according to the invention, causing the device to perform the method according to the invention. Therefore, the method according to the invention may be performed substantially automatically, or at least predominantly automatically.

Such a computer program is preferably loaded into a work memory of a data processor. The data processor is thus equipped to carry out the method of the invention. Further, the invention relates to a computer readable medium, such as a CD-ROM, at which the computer program may be stored. However, the computer program may also be presented over a network like the World Wide Web and can be downloaded into the work memory of a data processor from such a network.

It has to be noted that embodiments of the invention are described with reference to different subject matters. In particular, some embodiments are described with reference to method type claims whereas other embodiments are described with reference to apparatus type claims. However, a person skilled in the art will gather from the above and the following description that, unless other notified, in addition to any combination of features belonging to one type of subject matter also any combination between features relating to different subject matters is considered to be disclosed with this application.

The aspects defined above and further aspects, features and advantages of the present invention can also be derived from the examples of the embodiments to be described herein after and are explained with reference to examples of embodiments also shown in the figures, but to which the invention is not limited.

BRIEF DESCRIPTION OF THE DRAWINGS

FIG. 3 shows different tomography images.

FIG. 4 is a flowchart illustrating steps of a method according to the invention.

DETAILED DESCRIPTION OF EMBODIMENTS

Figure 1:
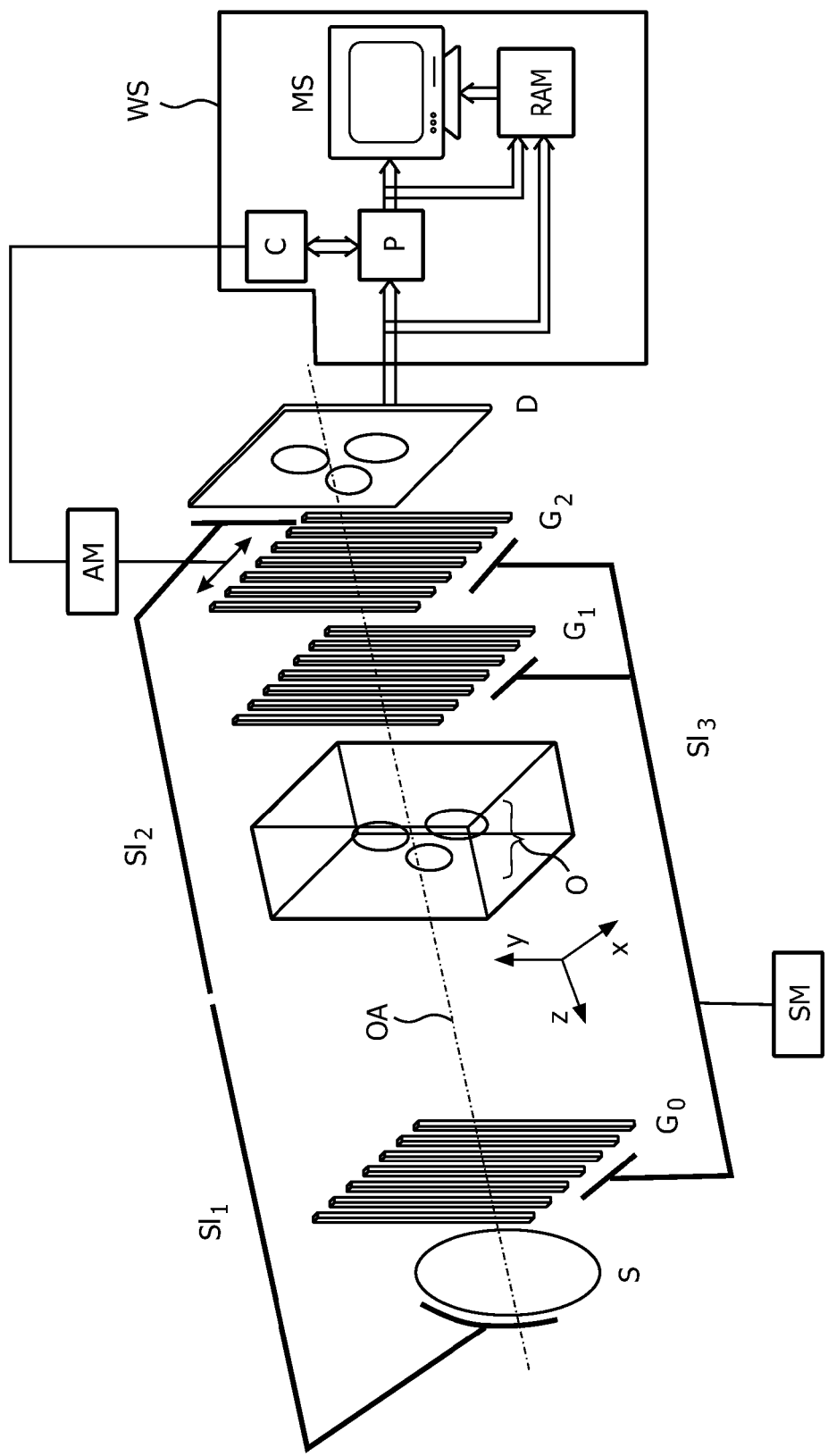
FIG. 1 is a schematically representation of a device for phase contrast imaging.

FIG. 1 is a schematically representation of a grating setup for a Talbot-Lau type hard-X-ray imaging interferometer, which may be used in accordance with the invention. The device will be described in the following in the context of a brief description of the functionality of the different parts of the device.

Using this kind of interferometer leads to the effect that interfering X-ray beams are not completely separated but merely sheared by a small angle, so that they pass through different, closely spaced parts of the sample. The hard-X-ray imaging interferometer comprises an incoherent X-ray source S, a source grating $G_0$ for achieving spatial beam coherence, a diffractive grating $G_1$ (herein also referred to as phase grating) having a plurality of equidistant X-ray absorbing strips extending in parallel in a direction normal to the interferometer's optical axis, which serves as a phase-shifting beam splitter and is placed in downstream direction behind the object, an absorber grating $G_2$ (also referred to as analyzer grating) and an X-ray detector D for detecting the image data of a Moiré interference pattern containing information about the phase shift of the deflected and phase-shifted X-ray beams after passing both the object O and the diffractive grating $G_1$.

Moreover, a processing means P of a workstation WS for recording the image data supplied by said radiation detector in a phase-stepping approach, a non-volatile read-access memory (RAM) for storing these data as well as a monitor screen MS or display for visualizing the recorded image data of the resulting Moiré interference pattern are provided.

To be able to move the source S, the source is mounted on a first slider $Sl_1$, whereas the detector D is mounted on a second slider $Sl_2$. With two sliders it may be possible to move only one, the source or the detector, to generate for example a 2D image of a ROI of an object. Moving both, the source and the detector, simultaneously may lead to 3D imaging of the ROI. Independent from the source and detector movement, the gratings may be arranged on a third slider $Sl_3$. By way of this, the whole grating arrangement may be easily moved out of the X-ray beam by means of for example a step motor SM. Usually, the grating arrangement may be movable within the X-ray beam or out of the X-ray beam in a plane perpendicular to a main direction or optical axis OA of the X-ray beam. It will be understood that also separate sliders may be utilized for the different gratings (like for the source and detector).

With respect to FIG. 1 it should be mentioned that the amount of the movement of the slider $Sl_3$ to move the grating arrangement out of the X-ray beam, may be at least one order greater than the amount of the movement of the grating $G_2$ within the X-ray beam induced by an actuator means AM to provide for the phase contrast imaging. For example, the movement of the slider may be a few mm or cm to position the grating arrangement within or outside the X-ray beam. On the other hand, the movement of the absorber grating $G_2$ may be only a few μm (micrometer).

The source grating $G_0$ creates an array of individually coherent, but mutually incoherent sources. Alternatively to $G_0$, a structured source can be used, where the apertures of $G_0$ are replaced by spatially restricted emission areas of an X-ray source, which is for example represented by a structured anode in an X-ray tube. The source grating can be even omitted if a micro-focus tube or a source with large spatial coherence, e.g., a synchrotron source is used. Distributed X-ray sources with CNT based emitters alternatively could also form an array of coherent sources. A phase object O in the beam path causes a slight refraction for each coherent subset of X-rays, which is proportional to the local phase gradient of the object. This small angular deviation results in changes of the locally transmitted intensity through the combination of gratings $G_1$ and $G_2$.

The phase grating $G_1$ acts as a beam splitter and divides an incoming X-ray beam essentially into the two first diffraction orders. Since the wavelength λ of the illuminating hard X-rays (which is typically in the order of below 0.1 nm) is much smaller than the grating pitch (which has a length of about 1 μm), the angle between two diffracted beams is very small. Downstream of the phase grating $G_1$, the diffracted beams interfere and form in certain distances known as fractional Talbot distances linear periodic fringe patterns with a periodicity g that equals half the phase grating period $p_1$ times the geometric magnification factor defined by the distances G0 to G1 and G0 to G2. It should be noted that the period and the lateral position of these fringes do not depend on the wavelength of the X-rays. Perturbations of the incident wave front, such as those induced by refraction on the object O in the beam, lead to local displacement of the fringes.

However, since phase grating pitch $p_1$ (and thus the spacing of the interference fringes) does not exceed a few micrometers, the imaging detector D placed in the detection plane may not have sufficient resolution to resolve the fringes. Therefore, the absorber grating $G_2$, which has the same periodicity and orientation as the fringes, acts as a transmission mask for imaging detector D and transforms local fringe positions into signal intensity variations, and is placed immediately in front of the plane of the imaging detector D. The detected signal profile hence contains quantitative information about the phase gradient $\partial\Phi(x,y)/\partial x$ of the object O. To separate this phase information from other contributions to the signal, such as absorption in the sample, inhomogeneous illumination or imperfections of the gratings, the phase-stepping approach may be adapted to this setup as well as a so-called blank scan, i.e., a scan without the object O.

Thus, two separate images of an object can be derived. The first one represents the intensity image that would have been received with no interferometer in the beam. It contains mainly absorption contrast and might also contain some in-line phase contrast caused by diffraction on the edges of the sample. The intensity signal of the second image is proportional to the phase shift gradient in the object, which is why it is called the differential phase contrast image (DPCI). The DPCI can be used to obtain the phase profile of the object by a simple one-dimensional integration.

The quality of the gratings used in such an interferometer set-up is crucial. To define the grating structures with sufficient accuracy, micro-fabrication techniques are conventionally used. It is essential that the gratings $G_1$ and $G_2$ have the correct ratio of periods. For a plane incoming wave, period $p_2$ of absorber grating $G_2$ should be half of that of phase grating $G_1$, whereas for a cone-shape incoming wave, a slight correction needs to be included. Microlithography techniques need to be used to define the grating line pattern on silicon substrates.

The further processing depends on the individual properties required. In particular, phase grating $G_1$ is characterized by low absorbing structures that introduce a phase shift $\Delta\phi$ of about $\pi$ radians to the passing X-ray waves, whereas absorber grating $G_2$ is characterized by highly absorbing grating lines. The actual size of the wave front's phase shift $\Delta\phi$ after transmitting a line structure of phase grating $G_1$ depends on the grating line thickness and on the wavelength $\lambda$ of the incident X-ray beam. If $G_1$ is irradiated by a plane wave, a periodic interference pattern of intensity is formed in the detector plane that changes as a function of distance d between phase grating $G_1$ and said detector plane. A periodic pattern of linear fringes perpendicular to the grating lines is for example observed at the first fractional Talbot distance, which is given by $d_1 = p_1^2/8\lambda$. The pitch of these fringes equals half of the periodicity of the phase grating $p_1$. The intensity or amplitude of these fringes depends on $\Delta\phi$ and shows a maximum modulation for $\Delta\phi = \pi[\text{rad}]$.

The structure height of phase grating $G_1$ which is needed to obtain the required phase shift is proportional to the photon energy used and the phase shift coefficient of the grating material. For 17.5 keV and a grating material of silicon, a height of 22 µm is an optimum.

The period $p_1$ of phase grating $G_1$ is close to 4 µm resulting in very high aspect ratios of the structures. The structures may be made by wet chemical etching in potassium hydroxide solution. As substrates, 250-µm thick silicon wafers with (110) orientation are used. The grating patterns are for example exposed using a high precision electron beam lithography process. The orientation of the lines is along the (112) direction with a precision of better than 0.1°, which results in an anisotropic etching with vertical side walls.

The fabrication of the absorber grating $G_2$ is even more challenging. Firstly, the period $p_2$ of the absorber grating has to be two times smaller than that of phase grating $G_1$, i.e., 2 µm, and secondly, no simple etching process exists to pattern highly absorbing materials with high aspect ratios. The structure height again depends on the photon energy and the absorption coefficient of the grating material At 17.5 keV, gold is used as an absorbing material. For a high contrast of the PCI signal a structure height of 10 µm is desirable. First, a silicon grating is patterned using the method described above. Then, the gaps of the grating are filled with gold by electro-deposition. Using a shadow evaporation process and selective wet etching, it is possible to let the gold grow from the bottom of the silicon grooves, as any deposition on the side walls or the silicon ridges would result in an incomplete filling of the grooves.

Having the source S and detector D arranged, for example at a C-arm or a CT gantry, or a source-detector arrangement rotatable around the object, i.e. at a combination of the sliders $Sl_1$ and $Sl_2$, with the grating arrangement in-between, will provide for the possibility to generate volumetric phase contrast images of an object. Therefore, the following aspects may be considered. Differential phase contrast projection data of a region of interest are acquired over an angular range of preferentially at least 180 degrees. Typical and preferred acquisition uses a circular path around the region of interest with a data acquisition over 360 degrees or 180 degrees plus the fan-angle of the detector.

Alternatively, data can be acquired using a helical path of the source detector arrangement around the region of interest. It is preferred that the direction of differentiation coincides with the tangent of the path of the X-ray source projected onto the detector. In the first processing step, the so-called pre-processing, the first derivative of these differential projection data is calculated numerically along the same direction (viz., the direction of the projected tangent to the source path).

These pre-processed projection data are back-projected into the region of interest. During the back-projection, two weighting functions can be applied to improve the image quality. The first one is a redundancy weighting function, which ensures that the contribution of redundant data sum up the reconstructed image in a normalized fashion. For a data acquisition with a circular path of 360 degrees, this weighting function can be as simple as a constant factor of ½. The second weighting that may be used is a density correction. For each object point within the region of interest and each pre-processed projection to be back-projected, the density of rays is calculated, squared and used as an additional back-projection weight. If the fan-angle of the system is small, or the region of interest to be reconstructed fits into a small fan-angle, this density compensation can be discarded in order to simplify the back-projection operation.

It is noted that the term "redundant" is used a little bit imprecisely in the area of cone-beam reconstruction. With reference to FIG. 1, the rotation axis is preferably aligned with the y-axis. In this geometry, any two data acquired during the scan are considered to be "redundant" for an object point within the region of interest if, firstly, the object point is located somewhere on the ray from the source to the detector that corresponds to this detection value, and secondly, the rays, projected parallel to the y-axis onto the zy-plane coincide.

Alternatively and prior to back-projection, the cone-beam data may be rebinned into pseudo-parallel (aka wedge) geometry. In this case, the density correction factor should not to be squared when used as back-projection weight.

A main idea of the invention is to apply the theory of local tomography to the problem of differential phase contrast CT.

As an example for a local tomography function, the approach starting from the local tomography function is outlined. There, the measurement provides line integrals for each source position, which is parameterized by a scalar variable s, and for each direction $\alpha$ (here and in the following, bold symbols relate to vectors):

$$D_f(s, \alpha) = \int_0^\infty f(y(s) + \alpha t) dt$$

and reconstructed is a local tomography function defined as $$g(x) = \mathcal{B} f(x) = \int_I \varphi(s, x) \frac{\partial^2}{\partial q^2} D_f(s, \beta(q, x)) \bigg|_{q=s} ds \text{ with}$$

-continued $$\beta(q, x) = \frac{x - y(q)}{|x - y(q)|}.$$

The weighting function φ takes care of redundancies. It is known that the local tomography function recovers local features of the object function f and that remaining non-local artifacts are an order of magnitude smaller.

For differential phase contrast CT, it is desired to make use of the fact that the measurement provides already a first derivative. However, the derivative is taken along a different coordinate. Specifically, for a planar detector with coordinates u and v, where v is the direction of the gratings, the derivative is measured in the direction of u:

$$\tilde{D}_f(s, u, v) = \frac{\partial}{\partial u} \int_0^\infty f(y(s) + \alpha(u, v)t) dt.$$

In order to apply the local tomography algorithm to differential phase contrast CT, the u-direction should be aligned with the tangent to the source path y(s). In this case, the reconstruction algorithm can be re-formulated using a relation to $$g(x) = Bf(x) = \int_I \frac{\varphi(s, x)}{(R(s) - x \cdot y(s)/R(s))^2} \frac{\partial}{\partial u} \tilde{D}_f(s, \alpha(u, v)) ds,$$

where R(s) denotes the distance of the source from the rotation axis. Note that in this formulation, only a derivative with respect to the detector coordinate appears, which is compensated during back-projection by a magnification factor that is well-known in cone-beam reconstruction methods.

Figure 2:
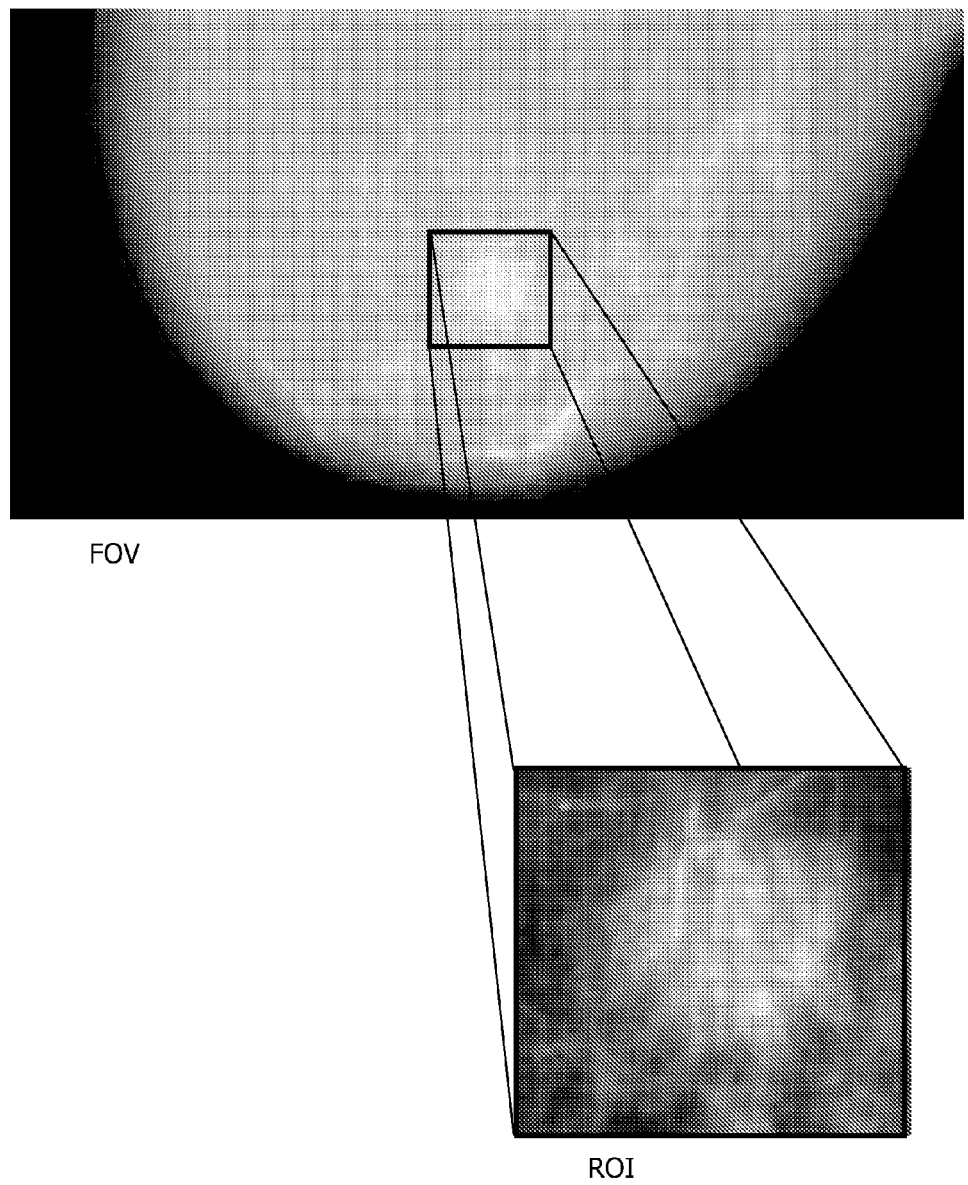
FIG. 2 illustrates an example of a field of view with a small region of interest.

FIG. 2 shows in the upper portion of the figure an exemplary absorption image generated without a grating arrangement, having a visible FOV. Further, there is illustrated a frame in the absorption image serving as a indication of a ROI, wherein the frame may be moved by command of an input device to a ROI. The lower portion of FIG. 2 illustrates a PCI image of said ROI, wherein in this example the PCI image may be enlarged and visualized separately from the absorption image. It is noted that the PCI image may also be an overlay on the absorption image, for example in the frame, and may also be illustrated in the same scale as the absorption image.

FIGS. 3A, 3B, and 3C show exemplarily reconstruction results obtained by the proposed method. Evidently, the local tomography approach recovers local structures quite well. At the same time, the artifacts caused by the non-perfect phase unwrapping at the object boundary are also present only locally. The image in FIG. 3C illustrates that the non-perfect phase unwrapping causes non-local artifacts in a conventional tomographic reconstruction of the differential data.

The flowchart in FIG. 4 illustrates the principle of the method for phase contrast imaging according to the invention. It will be understood that the steps described with respect to the method are major steps, wherein these major steps might be differentiated or divided into several sub-steps. Furthermore, there might be also sub-steps between these major steps. Therefore, a sub-step is only mentioned if that step is important for the understanding of the principles of the method according to the invention.

In step Sl, an X-ray scan may be performed with the arrangement of gratings driven out facilitating to produce a pure absorption image of the object in-between. The absorption image may be visualized on a screen so that the user can evaluate it together with an overlay of the current position of the arrangement of gratings in form of a frame having the same size as the FOV that is covered by the arrangement of gratings within the X-ray path.

In step S2, the user can move the frame via e.g. a computer mouse to a position within the absorption image he wants to do a PCI scan of a suspicious region. The slider $Sl_3$ of the grating arrangement and the sliders $Sl_1$ and $Sl_2$ of the source may be moved to the indicated position so that the grating arrangement covers an area on the plane perpendicular to the main X-ray beam path, the same as the frame within the absorption image on the computer screen.

In step S3, a PCI scan may be performed and visualized on the computer screen allowing the user to inspect it. This PCI scan may include the advantages of the local tomography.

If desired the PCI scan may be repeated in step S4 at other ROIs with the help of the same absorption image.

While the invention has been illustrated and described in detail in the drawings and afore-going description, such illustrations and descriptions are to be considered illustrative or exemplary and not restrictive, the invention is not limited to the disclosed embodiments.

Other variations to the disclosed embodiments can be understood and effected by those skilled in the art in practicing the claimed invention, from a study of the drawings, the disclosure and the appended claims. In the claims, the word 'comprising' does not exclude other elements or steps, and the indefinite article 'a' or 'an' does not exclude a plurality. A single processor or other unit may fulfill the functions of several items recited in the claims.

The mere fact that certain measures are recited and mutually different dependent claims does not indicate that a combination of these measures cannot be used to advantage. A computer program may be stored/distributed on a suitable medium such as an optical storage medium or a solid-state medium supplied together with or as a part of another hardware, but may also be distributed in other forms, such as via the internet or other wired or wireless telecommunication systems. Any reference signs in the claims should not be construed as limiting the scope.

LIST OF REFERENCE SIGNS

O object
S X-ray source
D X-ray detector
$G_0$ source grating
$G_1$ diffractive grating
$G_2$ absorber grating
AM actuator means
OA optical axis/main axis
C controlling means
P processing means
RAM read-access memory
WS workstation
MS monitor screen
$Sl_1$ first slider
$Sl_2$ second slider
$Sl_3$ third slider
FOV field of view
ROI region of interest

The invention claimed is:

1. A device for phase contrast imaging of an object, the device comprising:
   first, second, and third independently movable sliders;
   a source connected to the first slider and configured to issue an X-ray beam having an optical axis for producing absorption-based and phase contrast images;

a detector connected to the second slider and configured to detect the X-ray beam; and a grating arrangement including a plurality of gratings connected to the third slider between the object and the source and between the object and the detector for moving out of the optical axis of the X-ray beam to produce the absorption-based images, and within the optical axis of the X-ray beam to produce phase contrast images;

an input device configured to select a region-of-interest within the absorption-based image;

a variable aperture configured to adapt a field-of-view of the X-ray beam to the region-of-interest on the phase contrast images.

2. The device of claim 1, further comprising a processing unit configured for local tomography.

3. The device of claim 1, wherein the grating arrangement includes at least one of a source grating, a diffracting grating and an analyzer grating, wherein the source grating is located between the source and the object, and wherein the diffracting grating and the analyzer grating are located between the object and the detector.

4. The device of claim 1, wherein a width of the grating arrangement is smaller than a width of the X-ray beam, so that a portion of the X-ray beam passes through the grating arrangement, when the grating arrangement is located within the X-ray beam.

5. The device of claim 1, wherein the grating arrangement is movable in a plane perpendicular to a main direction of the X-ray beam.

6. The device of claim 1, further comprising an actuator configured to move the grating arrangement.

7. The device of claim 1, further comprising a monitor configured to visualize the absorption-based image and a phase contrast image of the region-of-interest.

8. The device of claim 1, wherein the input device moves the grating arrangement to cover the selected region-of-interest.

9. The device of claim 1, wherein the variable aperture changes a width of the X-ray beam to a width and a position of the grating arrangement.

10. A method for phase contrast imaging of an object, the method comprising the acts of:

providing a source connected to an independently movable first slider for issuing an X-ray beam having an optical axis through a portion of the object, a detector connected to an independently movable second slider and configured to detect the X-ray beam, a grating arrangement including a plurality of gratings connected to a third independently moving slider between the object and the source and between the object and the detector for moving within and out of the optical axis of the X-ray beam between the source and a detector;

producing absorption-based images by moving the grating arrangement out of the optical axis of the X-ray beam and phase contrast images by moving the grating arrangement within the optical axis of the X-ray beam;

selecting a region-of-interest within the absorption-based image;

adapting a field-of-view of the X-ray beam to the region-of-interest;

the detector detecting X-ray beam transmission data from different projection angles; and a processor generating an image based on the detected transmission data.

11. The method of claim 10, further comprising acts of performing a qualitative assessment of adjacent detector pixels, and visualizing the absorption-based image and a phase contrast image of the region-of-interest.

12. The method of claim 10, further comprising the act of: moving the grating arrangement out of the optical axis of the X-ray beam, generating an image of a portion of the object without the grating arrangement in the X-ray beam, and moving the grating arrangement between the source for the X-ray beam, the object and the detector so that a source grating is located between the source and the object, a diffracting grating and an analyzer grating are located between the object and the detector, and so that a portion of the X-ray beam passes through the grating arrangement.

13. The method of claim 10, wherein the grating arrangement is moved in a plane perpendicular to a direction of the X-ray beam.

14. The method of claim 10, further comprising the act of shifting at least one of the gratings for carrying out a phase stepping approach.

15. A non-transitory computer readable medium comprising computer instructions which, when executed by a processor, configure the processor to perform a method for phase contrast imaging of an object, the method comprising the acts of:

providing a source connected to a first slider for issuing an X-ray beam having an optical axis through a portion of the object, a detector connected to a second slider and configured to detect the X-ray beam, and a grating arrangement including a plurality of gratings connected to a third slider between the object and the source and between the object and the detector for moving within and out of the optical axis of the X-ray beam between the source and a detector, each slider is independently movable;

producing absorption-based images by moving the grating arrangement out of the optical axis of the X-ray beam and phase contrast images by moving the grating arrangement within the optical axis of the X-ray beam;

selecting a region-of-interest within the absorption-based image;

adapting a field-of-view of the X-ray beam to the region-of-interest;

moving the grating arrangement between the source for the X-ray beam, the object and the detector so that a source grating of the plurality of gratings is located between the source and the object, a diffracting grating and an analyzer grating of the plurality of gratings are located between the object and the detector, and so that a portion of the X-ray beam passes through the grating arrangement;

acquiring the X-ray beam from different projection angles by the detector; and generating an image of a portion of the object without the grating arrangement in the X-ray beam.

* * * * *